United States Patent [19]

Giordano et al.

[11] 4,336,396
[45] Jun. 22, 1982

[54] PROCESS FOR THE PREPARATION OF 4-[2-(DIMETHYLAMINO)-ETHOXY]2-METHYL-5-(1-METHYLETHYL)-PHENOL ESTERS AND THEIR SALTS

[75] Inventors: Claudio Giordano, Monza; Aldo Belli, Novara, both of Italy

[73] Assignee: Blasinachim S.p.A., Milan, Italy

[21] Appl. No.: 212,796

[22] Filed: Dec. 4, 1980

[30] Foreign Application Priority Data

Dec. 20, 1979 [IT] Italy ............................... 28251 A/79

[51] Int. Cl.³ ...................... C07C 79/46; C07C 67/42
[52] U.S. Cl. .................................... 560/20; 560/109; 560/131; 560/142; 564/354
[58] Field of Search ..................... 560/142, 131, 8, 20, 560/109; 564/354

[56] References Cited

U.S. PATENT DOCUMENTS 3,966,779 6/1976 Satzinger ........................... 560/142

FOREIGN PATENT DOCUMENTS 905738 7/1949 Fed. Rep. of Germany .
745070 2/1956 United Kingdom ................ 560/142
1164409 9/1969 United Kingdom .
1251237 10/1971 United Kingdom .
1374396 11/1974 United Kingdom .
1535531 12/1978 United Kingdom .

*Primary Examiner*—Natalie Trousof
*Assistant Examiner*—Frederick W. Pepper
*Attorney, Agent, or Firm*—Stevens, Davis, Miller & Mosher

[57] ABSTRACT

This invention relates to a process for the preparation of 4-[2-(dimethylamino)-ethoxy]-2-methyl-5-(1-methylethyl)-phenol esters (I) and their salts with organic and inorganic acids comprising the reaction of thymol with a salt of an 1-halo-dimethylaminoethane to obtain ethylamine-N,N-dimethyl-2-(thymyloxy) (II), the subsequent reaction of (II) with an acylating agent according to the Friedel and Kraft reaction to obtain 4-[2-(dimethylamino)-ethoxy]-2-methyl-5-(1-methylethyl)-1-acyl-benzene (III) and the oxidation of (III) to obtain the products (I) which, if desired, may be transformed in their salts with organic or inorganic acids.

This process allows to obtain the products (I) in high quality and quantity without isolating any intermediate product.

3 Claims, No Drawings

PROCESS FOR THE PREPARATION OF 4-[2-(DIMETHYLAMINO)-ETHOXY]2-METHYL-5-(1-METHYLETHYL)-PHENOL ESTERS AND THEIR SALTS

This invention relates to a process for the preparation of 4-[2-(dimethylamino)-ethoxy]-2-methyl-5-(1-methylethyl)-phenol esters (I) and their salts with organic and inorganic acids comprising the reaction of thymol with a salt of an 1-halo-dimethylaminoethane to obtain ethylamine-N,N-dimethyl-2-(thymyloxy) (II), the subsequent reaction of (II) with an acylating agent according to the Friedel and Kraft reaction to obtain 4-[2-(dimethylamino)-ethoxy]-2-methyl-5-(1-methylethyl)-1-acyl-benzene (III) and the oxidation of (III) to obtain the products (I) which, if desired, may be transformed in their salts with organic or inorganic acids.

More particularly this invention is directed to the preparation of the products having the following general formula:

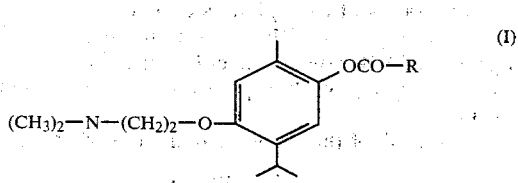

wherein R is a member of the group comprising one hydrogen atom, an alkyl radical and an aryl radical which may be substituted by one or groups which are inert towards the reaction mixture.

The product (I) wherein R is a methyl radical is known under the international common name "Moxisylyte" and it is used as a drug owing to its adrenergic blocking activity. The other products (I) are useful as intermediates for preparing Moxisylyte via transesterification.

According to the German Pat. No. 905.738 Moxisylyte is prepared by using thymol as starting material; the process involves eight steps and each intermediate has to be isolated and purified before of its use in the next step. Furthermore some reaction agents (i.e. nitrous acid and hydrogen sulfide) involve the use of very expensive antipollution means. In addition, one step of this process, more particularly the decomposition of the diazonium salts, is not selective because of the lacking of stabilizing substituents on the aromatic ring so that there are formed some coloured by-products which can be removed very difficulty. One further criticism is the low yield of each step.

Because of the time and expense required by this procedure a new process was desired.

It has been now found that thymol may be processed according to a simple procedure which allows to obtain the products (I) in high quality and quantity without isolating any intermediate product.

The schema of the new process of this invention is the following:

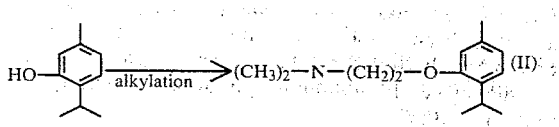

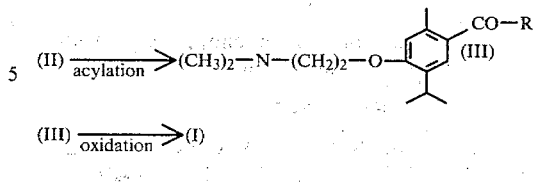

The alkylation of thymol is preferably carried out according to the phase transfer catalysis technology.

The liquid/liquid system is preferred to the liquid/solid system.

A liquid phase is formed by thymol alone or by thymol dissolved in a suitable organic solvent non-miscible with water. Another requirement for the organic solvent is that it has to be compatible with the acylation and the oxidation step. In case that the alkylation step is carried out without any organic solvent, the last one is added before the acylation step.

Suitable organic solvents according to this invention are toluene, benzene, xylenes, 1,2-dichloroethane, halotoluene, halobenzene, dichloromethane.

The other liquid phase consists of an alkaline solution, preferably sodium or potassium hydroxide in water.

As phase transfer catalyst may be used as "onium" salt, preferably an amonium salt, or a crown ether.

After completion of the reaction, the aqueous solution is discharged and the organic solution of the product (II) is submitted to acylation according to the Friedel-Kraft reaction in the presence of a product selected in the class of the Lewis and the Brönsted acids.

As acylating agent may be used the anhydride or an halide of the desired acid.

When the acyl-radical is the formyl radical the reaction is preferably carried out with a formyl radical forming reactant like dimethylformamide or N-methyl-N-phenyl-formamide in the presence of POCl$_3$.

The introduction of the acyl-radical in the para position with regard to the ethoxy-radical is very selective. In order to improve the yield, it has to be taken into account that the tertiary amino group of the product (II) sequestrates a certain amount of the Lewis or of the Brönsted-acid; from 1 to 2 moles, preferably 1.2 moles, of the Lewis or of the Brönsted-acid is used for 1 mole of the product (II).

After the reaction is over, the reaction mixture is added with an alkaline solution, preferably sodium hydroxide in water.

The inorganic layer is discharged and the organic solution is submitted to oxidation by choosing properly the conditions at which the oxidation of the acyl radical is maximized without affecting the tertiary amino group of the products (I and III).

Preferred oxidation agents are the peroxides selected in the group comprising hydrogen peroxide, m-chloroperbenzoic acid, perbenzoic acid, monopermaleic acid, monoperphtalic acid, peracetic acid and pertrifluoracetic acid.

In order to avoid its oxidation, the tertiary amino group of the products (I and III) has to be protected by means of an acid preferably selected in the group comprising the Lewis and the Brönsted acids.

The final product (I) is recovered and purified according to conventional procedures.

If desired the products (I) may be salified with organic or inorganic acids according to conventional procedures.

The final products (I) wherein R is different from CH₃ may be easily transformed into Moxisylyte by transesterification.

The following examples are intended only to illustrate but not to limit this invention.

EXAMPLE 1

(a) A solution of 1-chloro-2-dimethylaminoethane hydrochloride (540 g, 3.75 moles) is added slowly (2 h) and under vigorous stirring to a mixture of thymol (450 g, 3 moles) in toluene (4500 ml), 50% sodium hydroxide aqueous solution (2250 ml) and triethylbenzylamonium chloride (50 g), kept at 30° C.

After cooling, the inorganic layer is discharged whereas the organic layer is washed with water and dried over sodium sulphate.

The thus obtained solution contains 624.4 g (yield, 94.2%) of the product (II).

(b) Acetic anhydride (1300 ml) is added to 2430 ml of the solution obtained according to example 1a and containing 337 g (1.52 moles) of the product (II). To this solution is added 70% perchloric acid (340 ml) in about 30 minutes, mantaining the temperature below 45° C. The mixture is poured into water and made alkaline by addition of sodium hydroxide. The inorganic layer is discharged whereas the organic layer is washed with water and dried over sodium sulphate.

The organic solution contains 386.6 g (yield 97%) of the product (III) wherein R is CH₃ (IIIa).

(c) Trichloroacetic acid (480.7 g, 2.94 moles) and 80.4% meta-chloroperbenzoic acid (311.7 g, 1.47 moles) is added to a solution obtained according to example 1b.

The reaction mixture is mantained under stirring at 15° C. for 24 hours, then it is washed with diluted amonia, dried over sodium sulphate and the solvent is removed under reduced pressure.

The crude product is dissolved in anhydrous diethylether and the solution is saturated with hydrochloric acid gas. The solid product is collected by filtration, washed with diethylether and crystallized from isopropanol.

Yield, 287.5 g (0.91 moles; 62% of the theoretical amount) of Moxisylyte hydrochloride melting at 208°–210° C.

The overall yield as to thymol amounts to 56.6% of the theoretical amount.

EXAMPLE 2

In a 250 ml round-bottomed flask equipped with a refrigerant and a thermometer are introduced 20.8 g (0.08 moles) of IIIa, 140 ml of methylene chloride and 18.3 g (0.16 moles) of trifluoroacetic acid.

The solution is cooled at 15° C. under stirring and is added with 16.9 g (0.08 moles) of 82.3% m-chloroperbenzoic acid. The mixture is kept under stirring at 15° C. for 22 hours, then it is poured into water, made alkaline with sodium carbonate and extracted with diethylether.

The ethereal layer is dried over sodium sulphate and the solvent is removed by evaporation under reduced pressure. The solid residue weights 16.6 g. The yield of the crude Moxisylyte (titre 89%) is 67% of the theoretical amount.

The product has been identified by TLC, GLC, IR and NMR tests in comparison with a pure sample.

The crude Moxisylyte is dissolved in anhydrous diethylether and the solution thus obtained is satured with hydrochloric acid gas.

The solid product is collected by filtration, washed with ethylether and crystallized from isopropanol.

It is thus obtained the hydrochloride of Moxisylyte melting at 208°–210° C.

EXAMPLE 3

The process of example 2 is carried out by reacting 5.2 g (0.02 moles) of IIIa in 30 ml of 1,2-dichloroethane with 5.7 g (0.04 moles) of BF₃ etherate and with 4.2 g (0.02 moles) of 82.3% m-chloro-perbenzoic acid for 22 hours at 15° C. Yield, 39% of the theoretical amount of Moxisylyte.

EXAMPLE 4

The process of example 2 is carried out by reacting 5.2 (0.02 moles) of IIIa in methylene chloride (30 ml) with 6.6 g (0.04 moles) of trichloroacetic acid and with 4.2 g (0.02 moles) of 82.3% m-chloro-perbenzoic acid for 7 hours at the boiling temperature (40° C.). Yield, 36% of the theoretical amount of Moxisylyte.

EXAMPLE 5

The process of example 2 is carried out by reacting 5.2 g (0.02 moles) of IIIa in 1,2-dichloroethane (30 ml) with 6.6 g (0.04 moles) of trichloroacetic acid and with 7.6 g (0.02 moles) of 20% peracetic acid for 22 hours at 15° C.

Yield, 39% of the theoretical amount of Moxisylyte.

EXAMPLE 6

The process of example 2 is carried out by reacting 5.2 g (0.02 moles) of IIIa in acetic acid (30 ml) with 6.6 g (0.04 moles) of trichloroacetic acid and with 7.6 g (0.02 moles) of 20% peracetic acid for 22 hours at 15° C. Yield, 30% of the theoretical amount of Moxisylyte.

EXAMPLE 7

The process of example 2 is carried out by reacting 5.2 g (0.02 moles) of IIIa in 30 ml of a mixture (1:2 v/v) of water and acetic acid, with 6.6 g (0.04 moles) of trichloroacetic acid and with 2.3 g (0.02 moles) of 30% hydrogen peroxide for 22 hours at 15° C. Yield, 45% of the theoretical amount of Moxisylyte.

EXAMPLE 8

The process of example 2 is carried out by reacting 5.8 g (0.02 moles) of 4-[2-(dimethylamino)-ethoxy]-2-methyl-5-(1-methylethyl)-1-butyroyl-1-benzene (IIIb), prepared in a manner similar to the one disclosed by example 1b, in 1,2-dichloroethane (30 ml) with 6.6 g (0.04 moles) of trichloroacetic acid with 4.2 g (0.02 moles) of 82.3% m-chloroperbenzoic acid for 22 hours at 15° C.

Yield, 53% of the theoretical amount of 4-[2-(dimethylamino)-ethoxy]-2-methyl-5-(1-methylethyl)-phenol, butyroxy ester. (Ib).

The crude product is dissolved in methanol (30 ml) and added with an 30% aqueous solution of sodium hydroxide (10 ml), the solution is warmed at 40°–45° C. for 30 minutes.

The reaction mixture is diluted with water and shaked with toluene, the toluene layer is separated and washed with 10% sodium hydroxide solution.

The aqueous phases are brought together and acidified with concentrated hydrochloric acid and then extracted with diethylether. The aqueous layer is then made alkaline with amonium hydroxide and extracted with diethylether.

The ethereal extracts are collected, dried over anhydrous sodium sulphate and the solvent is removed by evaporation under reduced pressure. The residue is dissolved in toluene, added with 5 ml of acetic anhydride and the thus obtained solution is refluxed for some hours.

After cooling, the solution is washed with water and with sodium bicarbonate, dried over anhydrous sodium sulphate and the solvent is removed by evaporation under reduced pressure.

It is so obtained the product Ia. (Moxisylyte)

Yield, 51.5% of the theoretical amount as to product IIIb.

EXAMPLE 9

To a solution of 4-[2-(dimethylamino)-ethoxy]-2-methyl-5-(1-methylethyl)-1-(p-nitrobenzoyl)-benzene (IIIc) prepared in a manner similar to the one disclosed by example 1b (1 g; 0.0027 moles) in glacial acetic acid (25 ml) 96% sulfuric acid (15 g; 0.147 moles) and 38% peracetic acid (4 g; 0.02 moles) are added. The reaction mixture is stirred at room temperature for 15 hours, then it is poured into water and extracted with diethylether.

The aqueous layer is separated, made alkaline with sodium bicarbonate and extracted with diethylether.

The ethereal extracts are collected and the solvent is removed by evaporation under reduced pressure.

It is so obtained the 4-[2-(dimethylamino)-ethoxy]-2-methyl-5-(1-methylethyl)-phenol p-nitrobenzoxy ester (Ic) (0.4 g). Yield 31% of the theoretical amount.

What we claim is:

1. Process for the preparation of the products having the following formula:

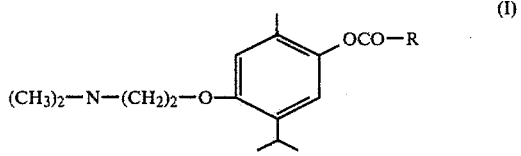

wherein R is a member selected from the group consisting of a hydrogen atom, an alkyl radical, an unsubstituted aryl radical and an aryl radical substituted by a nitro group, characterized in that
   (a) thymol is reacted with a salt of an 1-halo-dimethylaminoethane, and
   (b) the thus obtained ethylamine-N,N-dimethyl-2-(thymyloxy) is reacted with an acylating agent according to the Friedel and Kraft reaction, and
   (c) the thus obtained 4-[2-(dimethylamino)-ethoxy]-2-methyl-5-(1-methylethyl)-1-acyl-benzene is oxidated and, if desired, the thus obtained 4-[2-(dimethylamino)-ethoxy]-2-methyl-5-(1-methylethyl-phenol esters is added with an organic or inorganic acid.

2. Process according to claim 1 characterized in that no isolation and purification of the intermediate products occurs.

3. Process according to any one of claims 1 or 2 characterized in that the process is carried out in the presence of a solvent selected from the group comprising toluene, benzene, xylenes, 1,2-dichloroethane, halotoluene, halobenzene, dichloromethane.

* * * * *